(12) United States Patent
Seidenstricker et al.

(10) Patent No.: US 8,313,696 B2
(45) Date of Patent: Nov. 20, 2012

(54) TEST TAPE AND ANALYTICAL SYSTEM

(75) Inventors: Manfred Seidenstricker, Mannheim (DE); Karl Miltner, Frankenthal (DE); Edgar Baumann, Mannheim (DE); Konstanze Bogumil, Mannheim (DE); Wolfgang Heck, Ladenburg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1556 days.

(21) Appl. No.: 11/427,510

(22) Filed: Jun. 29, 2006

(65) Prior Publication Data

US 2007/0020143 A1 Jan. 25, 2007

(30) Foreign Application Priority Data

Jun. 29, 2005 (EP) ..................................... 05014014

(51) Int. Cl.
*G01N 21/00* (2006.01)
(52) U.S. Cl. ................. 422/67; 422/58; 422/66; 436/44
(58) Field of Classification Search .................... 422/58, 422/66, 67; 436/44
See application file for complete search history.

(56) References Cited

U.S. PATENT DOCUMENTS

| 4,204,767 | A | | 5/1980 | Kato et al. |
| 4,367,487 | A | | 1/1983 | Klein et al. |
| 4,954,319 | A | * | 9/1990 | Koizumi et al. ................. 422/67 |
| 5,077,010 | A | | 12/1991 | Ishizaka et al. |
| 2002/0041829 | A1 | | 4/2002 | Kowallis |
| 2005/0201897 | A1 | * | 9/2005 | Zimmer et al. ............ 422/82.05 |

FOREIGN PATENT DOCUMENTS

| DE | 103 43 896 A1 | | 4/2005 |
| EP | 0 371 572 A1 | | 6/1990 |
| EP | 1 304 162 A2 | | 4/2003 |
| WO | WO 2004/056269 A1 | | 7/2004 |
| WO | 2005032372 | * | 4/2005 |
| WO | WO 2005/047861 A2 | | 5/2005 |

* cited by examiner

*Primary Examiner* — Lyle Alexander
(74) *Attorney, Agent, or Firm* — Bose McKinney & Evans LLP

(57) ABSTRACT

A test tape for analyzing body fluids is provided comprising a flexible carrier tape and a plurality of test fields arranged spaced apart thereon for the detection of an analyte in the body fluid. The carrier tape is provided with indicator areas to register the distance and/or determine the position of the test tape or its components during tape transport.

16 Claims, 1 Drawing Sheet

TEST TAPE AND ANALYTICAL SYSTEM

REFERENCE TO RELATED APPLICATIONS

The present application is based on and claims priority to European Patent Application No. 05 014 014.4, filed Jun. 29, 2005, which is hereby incorporated by reference in its entirety.

TECHNICAL FIELD

The invention relates to a test tape for analyzing body fluids, comprising a flexible carrier tape having a plurality of test field arranged spaced apart thereon and adapted for the detection of an analyte in a sample of the body fluid. The invention further relates to an analytical system for processing such a test tape.

BACKGROUND

Test tapes for analyzing body fluids such as blood or urine can be used to detect components (analytes) in the body fluid. The tapes are generally provided in portable devices that operate automatically and can also be used by laymen to carry out the required analytical steps in a simple and rapid manner. A plurality of test fields each provided with a suitable test chemistry are arranged consecutively on a test tape wound on a reel, in contrast to conventional individual test strips. A sample of the body fluid is applied to a test field that is brought into an active position of an analytical system by advancing the tape, such as in a reel-to-reel configuration, in order to then be able to carry out a test, for example by means of an optical or electrochemical analysis. As in any reel-to-reel tape advancing system, fluctuations can occur in the moment of the mechanical load occurring on the tape transport path. Such fluctuations may be due to friction, increasing diameter of the used portion of the tape being wound on the drawing reel, and/or the resulting changes in speed. In an optimal system, the fluctuations should not have any effect on the exact positioning of the test fields at the active position for measurement or sample application. Nevertheless, if tape-positioning drives with positioning transmitters on their shafts or coupled machine components are used for advancing the tape, the mechanical tolerances of structural elements of the system, variations in the diameter of the tape reel, and tape slippage can all lead to deviations from the targeted position for a test field being brought into the active position.

In DE 103 43 896 A1, filed by the applicant and incorporated by reference herein in its entirety, various functional fields next to the test fields for a test tape are disclosed for purposes of providing user information or instructions for special instrument functions.

On the basis of the foregoing, the object of the invention is to further improve the prior art and to optimize the functionality of test tape type products, particularly in connection with positioning accuracy.

The combination of features stated in the claims are proposed to achieve this object.

SUMMARY

The premise of the present invention is to conduct a distance measurement or detect positional displacement directly from an object that is to be positioned. i.e. a test tape. Accordingly it is proposed according to the invention that the carrier tape of the test tape is provided with indicator areas to register the distance or indicate the position or amount of displacement during tape transport without contacting the test tape, such as with optical sensors. In this manner it is possible to directly determine the position of the test fields and any additional functional sections that may be present, independently of the tape drive to thus enable a substantially accurate and rapid positioning. As a result of such accurate positioning, the length of the test field can be made smaller and thus also the space required for the test tape can be reduced. In addition, with a shorter test field length, the required volume of the sample body fluid to be applied to the test field can be further reduced. The indicator areas on the test tape are also useful during tape manufacture with regard to accurately carrying out manufacturing processes such as cutting and gluing.

In one embodiment, each indicator area extends over a section of the tape between consecutive spaced apart test fields in the longitudinal direction. In contrast, the sections of the tape comprising the test fields are kept free of any indicators. In other embodiments, the indicator areas run continuously along the tape, such as on the underside of the tape or along at least one edge.

Typically, the indicator areas are configured for contactless position sensing, such as with one or more optical sensors.

According to one embodiment, the test tape of the present invention is adapted to bring successive test fields into an active position within an analytical system by position-controlled tape advancement.

In other embodiments, the indicator areas are adapted to indicate a distance scale that can be scanned incrementally. This can be simply achieved when the indicator areas are formed, for example, by a raster strip comprising alternation optically distinct segments, such as light and dark segments, or transparent and opaque segments. In yet other embodiments, one of the alternating segments is made of metal and can be scanned electrically or magnetically. In any event, suitable alternating segments are sensed comparatively with respect to each other.

In order to also obtain information about the direction of movement during tape transport, in one embodiment the indicator areas comprise two raster strips that are parallel to one another and staggered relative to one another in the longitudinal direction and can thus be scanned with a directionally-dependent phase shift.

In yet other embodiments, the indicator areas comprise a coded distance scale, for example in the grey code.

In yet other embodiments, the test tape is provided in a tape cassette comprising a supply reel holding the portion of test tape with unused test fields and a waste reel for receiving the portion of test tape with used test fields.

The present invention also relates to an analytical system in which embodiments of the test tape are employed. In one embodiment, the system comprises a test tape having test fields for detecting an analyte in a body fluid, the test fields being spaced apart along the tape by indicator areas, a tape transport device for transporting the tape to position the test fields in an active position, and a position detection device comprising sensor means, the position detection device being configured to scan the indicator areas on the test tape to detect the tape position and/or register the transported distance or displacement during tape transport.

In order to allow the most effective drive control, in one embodiment the position detection device is configured to detect the direction of transport and/or the distance travelled during tape transport, directly from the test tape.

In other embodiments, the position detection device is located at a predetermined distance along the tape from a measuring unit that analyzes sample applied to the test fields.

In yet other embodiments, a self-synchronizing read-out is provided when the position detection device has sensor mean positioned at the side of the test tape for scanning the indicator areas during tape transport in a contact-free manner, e.g. using optical sensors.

In yet other embodiments, the tape transport device has a drive control for transporting the test tape to put the test fields into the predetermined active position, and the control is operatively coupled to the position detection device. This allows a rapid and accurate movement to the active position thus also reducing the waiting times for the user.

In order to further support a robust braking, in one embodiment the tape transport device comprises a drive unit that can be actuated in an opposite direction that the normal tape advancement direction. The actuation is performed as a function of an output signal of the position detection device. In other embodiments, the tape advancement can be actively and robustly braked until standstill by briefly applying an electric inverse voltage to the drive unit, i.e. by reversing the voltage at a suitable voltage level.

These and other features and advantages of the present invention will be more fully understood from the following detailed description of the invention taken together with the accompanying claims. It is noted that the scope of the claims is definitely by the recitations therein and not by the specific discussion of the features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment(s) of the present invention.

In order that the invention may be more readily understood, reference is made to the following examples, which are intended to illustrate the invention, but not limit the scope therof.

DETAILED DESCRIPTION

Figure 1:
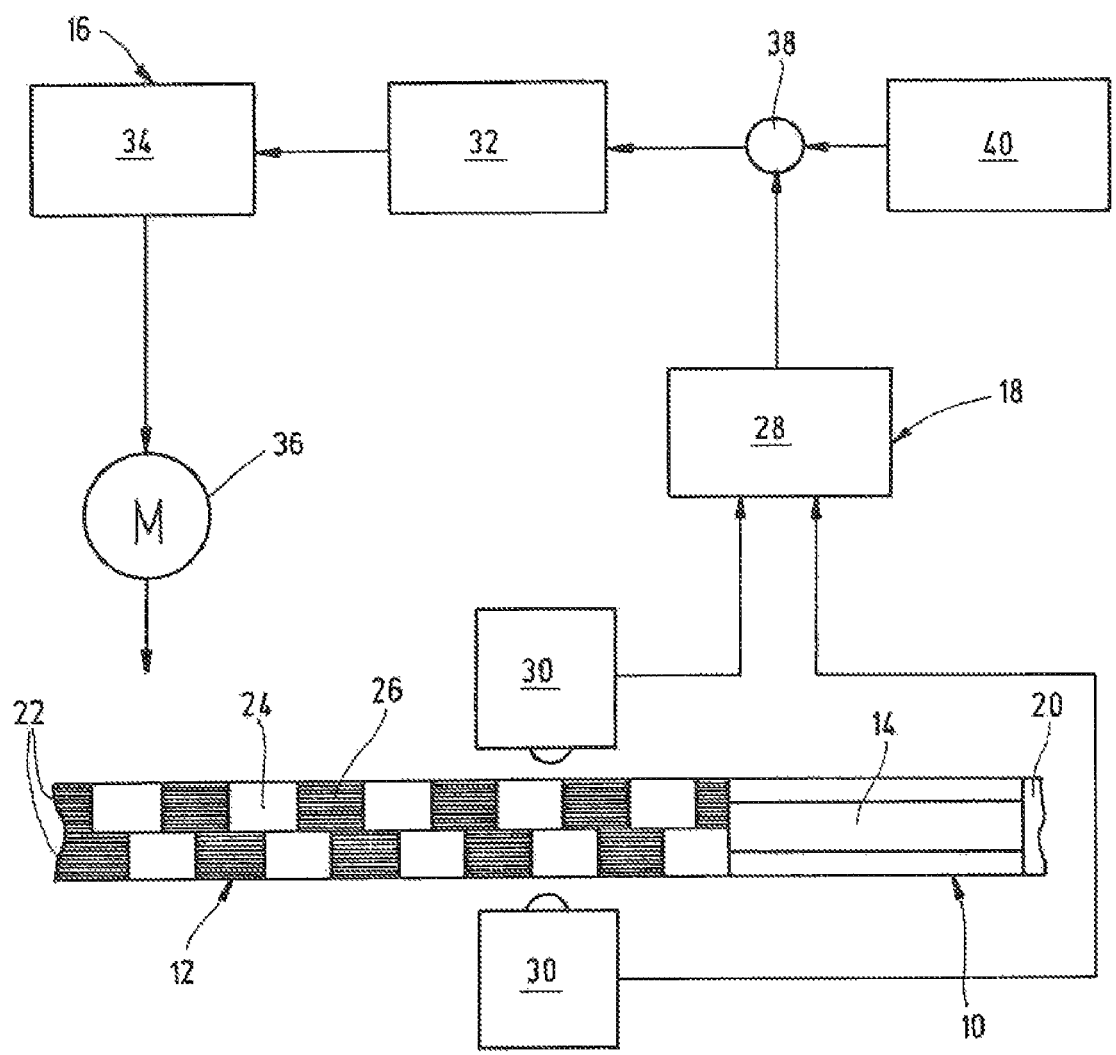
FIG. 1 shows a block diagram of an embodiment of an analytical system for processing a test tape having indicator areas.

The embodiment of an analytical system shown in FIG. 1 comprises a test tape 10 having indicator areas 12 and test fields 14, a tape transport device 16 for successively positioning the test fields in an active position and a position detection (or distance registering) device 18 that scans the indicator areas 12. The position detection device 18 actuates the tape transport device 16 in accordance with the tape position detected from the indicator areas.

As shown in the embodiment of FIG. 1, the test tape 10 has a continuous carrier foil 20 which carries a plurality of test fields 14 arranged spaced apart in the longitudinal direction of the tape. The test fields 14 may be provided with dry reagents for detecting a component or analyte in a sample of body fluid applied to a test field. In one embodiment, the test fields are configured to determine the concentration of sugar (e.g. glucose) from whole blood or serum samples.

In one embodiment, the indicator areas 12 are applied to the carrier foil 20 in the sections between the test fields 14. As shown in FIG. 1, two parallel raster strips 22 that are staggered relative to one another along the tape are provided. They consist of alternating light (or transparent) segments 24, and dark (or opaque) segments 26, and form scannable distance scales that are phase-shifted relative to one another as explained in more detail below.

In one embodiment, the position detection device 18 has a signal processing component 28 which on the input side interacts with electro-optical sensors 30. The sensors 30 may be positioned on a broad side of the test tape 10 to scan the raster strips 22 for light barriers (such as caused by the dark or opaque segments) such that periodic electrical impulses corresponding to the light barriers are emitted during tape transport to a counter in the signal processing component 28. As a result of the tape transport, the impulses are registered with a 90° phase shift which, in addition to indicating the distance travelled, also indicates the direction of movement directly on the tape 10.

In certain embodiments, the tape transport device 16 comprises a controller 32 with a correcting element 34 for actuating the positioning drive 36 (shown in FIG. 2) of the test tape 10. A comparator 38 can be used to communicate to the controller 32 the difference between a preset distance (corresponding to an accurate advancement of the test tape) and the output value of the position detection device 18. This allows a test field 14 to be rapidly and accurately positioned at the active position for analyzing an applied sample.

In such embodiments, the position of the test tape is detected or registered as a result of detecting or registering the displacement of the segments 24, 26 past the sensors 30 during tape transport. In other embodiments, the segments 24, 26 in the raster strips 22 have a constant length or a predetermined spacing in the longitudinal direction. As a result, the number of beginnings and/or ends of the impulses from detected light barriers can be counted by the counter of the signal processing component 28, which count is thus directly proportional to the distance the tape 10 has travelled.

As shown in the embodiment of FIG. 1, a distance preset component 40 can be provided to send preset counts to the comparator 38 in chronological sequence. The comparator then calculates the difference between the preset counts and the count from the signal processing component 28. This difference gives the controller 32 the measure for the actuation of the drive.

In other embodiments not shown, the test tape 10 my be configured to indicate an absolute start position from which incremental advancement distance can be determined. The carrier foil 20 can for example be provided with a light (or transparent/translucent) portion for a certain distance without a distinguishing dark (or opaque) segment 26 (such as from the raster strips). The tape 10 with the light portion is advanced past the sensors 30 until a first dark segment 26 is reached, which thus indicates an absolute start position which is known to the device 18 and from which point advancement increments are counted as described above.

It will be understood by those of ordinary skill in the art that the indicator areas can also be provided more simplistically than the rast strips 22 shown in FIG. 1, in which the segments are staggered. For example, a single raster strip 22 may be provided with a single track of alternating segments 24, 26. Alternatively, the carrier foil 20 can be provided with indicator areas comprising a base light (or transparent/translucent) segment 24 and one or more periodic dark (or opaque) segments provided therealong. In any event, the position detection device 18 is configured to register or detect the segments 24, 26 of any more simple embodiment substantially the same as described above.

Figure 2:
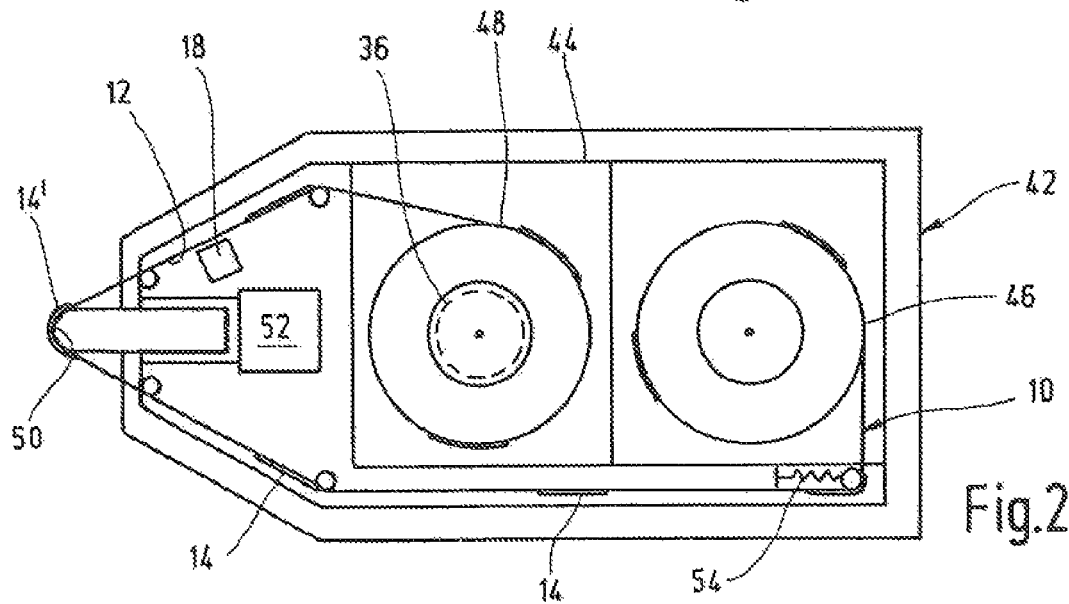
FIG. 2 shows an embodiment of an analytical system comprising a portable instrument in a simplified sectional diagram.

FIG. 2 illustrates the processing of a test tape 10 in a cassette device 42 as a portable analytical system. The cassette device 42 has a supply reel 46 on which is wound test tape having unused test fields 14, and a drawing or rast reel 48 on which is wound test tape having used test fields 14 and comprising a drive 36 for advancing the tape 10 from one reel to the other via the active position for the test fields. Sample liquid (e.g. blood) can be applied to the test fields 14 at a deflection tip 50. In one embodiment, an analyte (e.g. glucose) in the sample liquid is detected by reflection photometric measurement using the measuring unit 52. (Other possible measuring techniques, such as electrochemical methods, are known in the art and it will be understood by those of ordinary skill in the art that the particular measurement method employed by the system is not limiting of the invention). In the embodiment of FIG. 2, the measuring unit 52 is optically coupled via the tip 50, which is designed as a light guide, through the transparent carrier foil 20 to an active test field 14', e.g. a test field located in the active position. The test fields 14 can be successively brought into use by appropriate tape advance. In this manner multiple tests for patient self-monitoring can be carried out without having to handle or exchange disposable test strips.

As shown in the embodiment of FIG. 2, the position of the test field 14 at the guide tip 50 is determined by a position detection device 18 which is spaced apart therefrom by a defined displacement or distance offset. When the tap 10 is advanced and a predetermined number of segments 24, 26 are detected or registered by the position detection device 18, an active test field 14' is also positioned at the active position above the optical measuring unit 52 (taking into account the distance offset from tip 50). The distance offset allows a straightening out of instrument functions at a critical site from an optical (light sealing) and mechanical point of view (limited structural space in the area of the tip 50). In other embodiments, the position detection device 18 enables the position of the tape 10 to be also monitored during measurement on the active test field 14'.

Generally, the tape transport can only occur under tension due to the flexible carrier tape 20. In the embodiment shown in FIG. 2, advancement of the tape 10 occurs by turning the drawing reel 48 in a clockwise direction. In order to achieve a rapid active braking before reaching the receiving position, the drive 36 can be briefly driven with an opposite drive moment, i.e. high braking moment. This is achieved by applying a controlled counter voltage by means of the control device 32, 34 whereby a spring loaded tape tensioner 54 on the side of the supply reel 46 ensures the necessary tape back-tension. On the basis of the indicator areas 12, the position detection device 18 also detects any reversal of the direction of tape movement due to an excessive opposing drive moment and switches off the drive in time so that the active position is reached by a test field 14 without overshooting. It is basically also possible that when the active position is passed, the tape is moved back the required distance.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features, that my or may not be utilized in a particular embodiment of the present invention.

For the purposes of describing and defining the present invention it is noted that the term "substantially" is utilized herein to represent the inherent degree of uncertainty that my be attributed to any quantitive comparison, value, measurement, or other representation. The term "substantially" is also utilized herein to represent the degree by which a quantitave representation may vary from a stated reference without resulting in a change in the basic function of the subject matter at issue, Having described the invention in detail and by reference to specific embodiments thereof, it will be apparent that modification and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. Analytical system for analyzing body fluids comprising:
a flexible carrier tape,
a plurality of test fields arranged spaced apart on the carrier tape and adapted for the detection of an analyte in the body fluid,
the carrier tape further comprising indicator areas for contactless detection or registering of the position of the test tape, wherein each indicator area extends in the longitudal direction of the tape in a section of the tape between consecutive spaced apart test fields, the indicator areas having a portion thereof poositioned centrally relative to the side edges of the test tape, the indicator areas forming distance scales configured for detection of the distance traveled by the tape during transport of the tape in an analytical system; and
a position detection device configured to scan the indicator areas to determine distance traveled by the test tape during transport of the tape.

2. Test tape according to claim 1, wherein sections of the carrier tape comprising the test fields contain no indicators.

3. Test tape according to claim 1, wherein the indicator areas form an incremental position scale.

4. Test tape according to claim 1, wherein the contactless position detection or registering comprises an electro-optical sensing configuration.

5. Test tape according to claim 1, wherein the test tape is configured to bring successive test fields into an active position within an analytical system by position-controlled tape advancement.

6. Test tape according to claim 1, wherein the indicator areas are formed by at least one raster strip comprising alternating optically distinguishable segments.

7. Test tape according to claim 6, wherein the optically distinguishable segments comprise light and dark segments or transparent/translucent and opaque segments.

8. Test tape according to claim 6, wherein the indicator areas comprise two parallel raster strips that are staggered relative to one another in the longitudinal direction.

9. Tape cassette for magaznization of the test tape according to claim 1, comprising a supply reel having a portion of the test tape having unused test fields, and a waste reel configured to receive a portion of the test tape having used test fields.

10. Analytical system comprising:
a test tape having distance scales and a plurality of spaced apart test fields for detecting an analyte in a sample of a body fluid, the distance scales being provided in sections of the tape between consecutive spaced apart test fields, a tape transport device for positioning the test fields in an active position of the system, and a position detection device comprising sensor means and configured to scan the distance scales on the test tape in order to measure the distance traveled by the tape during transport thereof, whereby the test fields can be accurately positioned in the active position based upon the measured distance.

11. Analytical system according to claim 10, wherein the position detection device is further configured to detect the direction of movement and the distance travelled during tape transport directly from the test tape.

12. Analytical system according to claim 10, wherein the position detection device is located a predetermined distance along the tape from a measuring unit that analyzes a sample applied to an active test field.

13. Analytical system according to claim 10, wherein the sensor means is positioned at least one side of the test tape and is configured for contactless scanning of the indicator areas during tape transport.

14. Analytical system according to claim 13, wherein the contactless scanning comprises an electro-optical sensing configuration.

15. Analytical system according to claim 10, wherein the tape transport device comprises a drive control configured to transport the test tape into an active position, the drive control being operatively coupled to the position detection device.

16. Analytical system according to claim 15, wherein the tape transport device further comprises a drive unit configured to be actuated in an opposite direction than a tape advancement direction, the opposite actuation occurring as a function of an output signal of the position detection device.

* * * * *